(12) United States Patent
Nierlich et al.

(10) Patent No.: US 7,002,053 B2
(45) Date of Patent: Feb. 21, 2006

(54) METHOD FOR PREPARING HIGH-PURITY DIISOBUTENE

(75) Inventors: Franz Nierlich, Marl (DE); Lothar Kerker, Duelmen (DE); Udo Peters, Marl (DE); Wilfried Büschken, Haltern (DE); Andreas Beckmann, Recklinghausen (DE)

(73) Assignee: OXENO Olefinchemie GmbH, Marl (DE)

( * ) Notice: Subject to any disclaimer, the term of this patent is extended or adjusted under 35 U.S.C. 154(b) by 293 days.

(21) Appl. No.: 10/467,844

(22) PCT Filed: Dec. 28, 2001

(86) PCT No.: PCT/EP01/15365

§ 371 (c)(1),
(2), (4) Date: Aug. 13, 2003

(87) PCT Pub. No.: WO02/064531

PCT Pub. Date: Aug. 22, 2002

(65) Prior Publication Data

US 2004/0054246 A1 Mar. 18, 2004

(30) Foreign Application Priority Data

Feb. 13, 2001 (DE) ............... 101 06 593
Mar. 20, 2001 (DE) ............... 101 13 381

(51) Int. Cl.
*C07C 2/24* (2006.01)
*C07C 2/02* (2006.01)
*C07C 61/00* (2006.01)
*C07C 211/00* (2006.01)

(52) U.S. Cl. ............ 585/515; 585/510; 585/516; 585/520; 585/526; 562/400; 564/1

(58) Field of Classification Search ........... 585/510, 585/515, 516, 520, 526; 562/400; 564/1
See application file for complete search history.

(56) References Cited

U.S. PATENT DOCUMENTS

| | | | | | |
|---|---|---|---|---|---|
| 3,955,938 | A | * | 5/1976 | Graham et al. ............... | 44/305 |
| 4,066,713 | A | * | 1/1978 | Faraci et al. ................ | 585/811 |
| 4,100,220 | A | | 7/1978 | Bowman et al. | |
| 4,161,496 | A | * | 7/1979 | Humbert et al. ............ | 585/836 |
| 4,267,075 | A | * | 5/1981 | Schaper et al. .............. | 512/26 |
| 4,436,936 | A | * | 3/1984 | Howell ....................... | 564/409 |

OTHER PUBLICATIONS

U.S. Appl. No. 10/790,706, filed Mar. 3, 2004, Beckmann et al.
U.S. Appl. No. 10/805,256, filed Mar. 22, 2004, Beckmann et al.
U.S. Appl. No. 10/790,707, filed Mar. 3, 2004, Beckmann et al.
U.S. Appl. No. 10/487,950, filed Mar. 5, 2004, Beckmann et al.
U.S. Appl. No. 10/634,894, filed Aug. 6, 2003, Beckmann et al.
U.S. Appl. No. 10/543,148, filed Jul. 25, 2005, Peters et al.
U.S. Appl. No. 10/519,397, filed Jan. 3, 2005, Obenaus et al.

* cited by examiner

*Primary Examiner*—Walter D. Griffin
*Assistant Examiner*—In Suk Bullock
(74) *Attorney, Agent, or Firm*—Oblon, Spivak, McClelland, Maier & Neustadt, P.C.

(57) ABSTRACT

The invention relates to a process for preparing high-purity diisobutene by reaction of isobutene or isobutene-containing hydrocarbon mixtures over a solid acidic ion-exchange resin containing sulfonic acid groups whose protons have been partly replaced by metal ions and to the use of the diisobutene.

14 Claims, No Drawings

METHOD FOR PREPARING HIGH-PURITY DIISOBUTENE

The invention relates to a process for preparing high-purity diisobutene from isobutene or isobutene-containing hydrocarbon mixtures.

Diisobutene, namely a mixture of 2,4,4-trimethyl-1-pentene and 2,4,4-trimethyl-2-pentene, is hydrogenated industrially to produce 2,2,4-trimethylpentane. Owing to its high octane number, this hydrocarbon is a prized carburetor fuel component. For this purpose, it is also possible to use diisobutene mixtures comprising other $C_8$ isomers or hydrocarbons having different numbers of carbon atoms. On the other hand, use in syntheses requires diisobutene of higher purity. Thus, high-purity mixtures are required for preparing 3,5,5-trimethylhexanal by hydroformylation. This aldehyde can be oxidized to give the corresponding carboxylic acid which is used for preparing peroxides, lubricants and dryers. Diisobutene is also used for the alkylation of phenols. The alkylaromatics formed in this way are intermediates for the production of detergents.

The oligomerization of isobutene can be catalyzed by Lewis acids, Brönsted acids or coordination compounds, in particular those of nickel. Such oligomerization reactions form oligomers having different molar masses, since lower oligomers which have already been formed ($C_8$-, $C_{12}$-olefins) can react with isobutene or other oligomers to give higher molecular weight olefins. If the starting materials also contain n-butenes, cooligomers can also be present in the product.

For this reason, the economical preparation of 2,4,4-trimethylpentenes (1 and/or 2) by dimerization of isobutene requires not only a good space-time yield but also a high $C_8$ selectivity and a high $C_8$ isomer purity. These parameters can be influenced by the type of catalyst used and the reaction conditions. The catalyst used must therefore catalyze neither skeletal isomerization during $C_8$ formation nor isomerization of the $C_8$-olefin already formed. Otherwise, the product formed will have only limited suitability for chemical syntheses.

The oligomerization can in principle be carried out homogeneously, i.e. using catalysts which are soluble in the reaction mixture, or heterogeneously, i.e. using catalysts which are insoluble in the reaction mixture. The disadvantage of homogeneous processes is that the catalyst leaves the reactor together with the reaction products and unreacted starting materials from which it has to be separated, worked up and disposed of or recirculated.

Most industrial processes therefore employ catalysts which are present in a fixed bed so that complicated catalyst separation becomes unnecessary. Most known fixed-bed catalysts belong to one of the following groups:
  a) mineral acids (e.g. sulfuric acid or phosphoric acid) on a support material (e.g. aluminum oxide or silicon dioxide)
  b) zeolites or other aluminosilicates with or without further metal(s), in particular transition metals
  c) acidic ion-exchange resins.

Mineral acids on supports are not suitable for the preparation of a high-purity mixture of the two 2,4,4-trimethylpentenes from isobutene, since they also catalyze skeletal rearrangements.

In EP 0 224 220, oligomerization of butene is carried out over a bismuth- and/or lead-doped zeolite catalyst. Here, the $C_8$ fraction contains more than 4% of undesired 2,3,4-trimethylpentenes. The oligomerization of isobutene over an X-ray-amorphous aluminosilicate is disclosed in EP 0 536 839 A2. Here, a loss of 2,2,4-trimethylpentenes by skeletal isomerization cannot be avoided even at the mild temperatures of 60–65° C.

Oligomerization of isobutene over an X-ray-amorphous nickel aluminosilicate is described in WO 93/06926. Here, undiluted isobutene is reacted at 60° C. The product spectrum shows that the $C_8$ selectivity is not particularly high. At an isobutene conversion of 15–20%, the $C_8$ selectivity is 85–86%, and at a conversion of 75%, only 72%.

In EP 0 417 407 A1, shaped bodies made of strongly acidic ion exchangers are used as catalyst for the oligomerization of isobutene. Some of these ion exchangers are treated with acid after their preparation in order to achieve an increased acidity. The yield of dimers of 93–96% is good. However, the composition of the $C_8$ fraction is not disclosed.

The use of moderators, for example methyl tert-butyl ether or tert-butanol, for adjusting the catalyst activity of acidic ion-exchange resins is found to have an advantageous effect on the product spectrum. The major disadvantages are that the moderator has to be separated from the product and that it is difficult to obtain a $C_8$-olefin mixture which is free of traces of the moderator.

U.S. Pat. No. 4,447,668 describes a coupled process in which MTBE is firstly cleaved over an acidic ion exchanger to form high-purity isobutene and methanol. The isobutene obtained in this way can optionally be oligomerized in a liquid phase over an acidic ion-exchange resin in the presence of methyl tert-butyl ether (MTBE). MTBE serves as solvent and controls the catalyst activity. Distilling off the MTBE leaves an oligomer which comprises up to 97% of diisobutene. No more detailed information is given about the oligomerization catalyst used or about the isomer composition of the $C_8$ fraction.

U.S. Pat. No. 5,877,372 describes a process for preparing "isooctane" (hydrogenated diisobutene) from tert-butanol. One step in this process is the oligomerization of isobutene over an acidic ion-exchange resin. To set the desired catalyst activity, the starting material for this step contains 1–30% of tert-butanol and, to increase the $C_8$-olefin selectivity, 30–80% of "isooctane". The reaction mixture is fractionally distilled to give a top product comprising tert-butanol and unreacted isobutene and a bottom product comprising "isooctane" and the higher oligomers. Over 90% of the oligomer fraction is diisobutene. This mixture is hydrogenated to give "isooctane" containing a few percent of higher molecular weight, saturated hydrocarbons, part of which is recirculated to the dimerization step. Catalysts used are commercial, acidic ion-exchange resins.

Separating the $C_8$-olefins from an oligomer obtained by this process requires costly distillation apparatus, since the boiling points of "isooctane" 2,2,4-trimethylpentane (99° C.), 2,4,4-trimethyl-1-pentene (100–102° C.) and 2,4,4-trimethyl-2-pentene (102–105° C.) are close together. In addition, the composition of the $C_8$-olefin fraction prepared by this process is not known.

GB 2 325 237 A describes a process for preparing a diisobutene-containing mixture, in which isobutene is reacted over an acidic ion-exchange resin in the presence of methanol and methyl tert-butyl ether. The reaction is carried out in two reactors connected in series with intermediate separation of the products after the first reactor. The product mixture from the two reactors comprises, after the low boilers have been separated off, up to 90% of dimer, higher oligomers and the methyl ether derived from the dimer. Here too, the object is to obtain a high-octane component or a precursor for carburetor fuels. On the other hand, the isolation of high-purity diisobutene is neither envisaged nor described.

Since the known processes are not entirely satisfactory in terms of the $C_8$ selectivity and/or the purity of the $C_8$ fraction, it is an object of the invention to develop an improved process for preparing a high-purity mixture of the two isomeric 2,4,4-trimethylpentenes (1 and/or 2).

It has surprisingly been found that, in the oligomerization of isobutene in a liquid phase over an acidic ion-exchange resin containing sulfonic acid groups, the selectivity of $C_8$-olefin formation and the 2,4,4-trimethylpentene content of the $C_8$ fraction is increased when part of the protons is replaced by metal ions.

The invention accordingly provides a process for preparing high-purity diisobutene by reaction of isobutene or isobutene-containing hydrocarbon mixtures over a solid acidic ion-exchange resin containing sulfonic acid groups whose protons have been partly replaced by metal ions.

Acidic ion-exchange resins are usable catalysts for the oligomerization of isobutene only when they have a certain minimum acidity. Thus, resins containing carboxylic acid groups are not acidic enough and are therefore not suitable as catalysts. Suitable resins contain sulfonic acid groups. As mentioned above, reaction of isobutene over sulfonated ion-exchange resins results in formation of by-products if a regulator is not continually fed in together with the starting material.

It is known from the literature that the acid strength of ion exchangers containing sulfonic acid groups can be reduced by partial ion exchange (Structure-breaking Effect of Metal Ions influencing the Acidity of an Anhydrous Acid, C. Buttersack, H. Widdecke, J. Klein, Journal of Molecular Catalysis, 40 (1987) 23–25). However, it was not obvious that such a modified ion-exchange resin could be used advantageously for the oligomerization of isobutene.

The process of the invention is carried out using solid sulfonated ion-exchange resins in which from 30 to 90% of the protons of the sulfonic acid groups, preferably from 50 to 80%, have been replaced by metal ions. As metal ions replacing the protons, it is possible to use alkali metal, alkaline earth metal, chromium, manganese, iron, cobalt, nickel, zinc and aluminum ions and also ions of the lanthanide group. Preference is given to using alkali metal ions, in particular sodium ions, for this purpose. It is also possible for the resin to be loaded with two or more different metal ions.

Suitable ion-exchange resins are, for example, ones obtained by sulfonation of phenol/aldehyde condensates or of cooligomers of aromatic vinyl compounds. Examples of aromatic vinyl compounds for preparing the cooligomers are: styrene, vinyltoluene, vinylnaphthalene, vinylethylbenzene, methylstyrene, vinylchlorobenzene, vinylxylene and divinylbenzene. Particular preference is given to using the cooligomers formed by reaction of styrene with divinylbenzene as precursor for the preparation of ion-exchange resins containing sulfonic acid groups. The resins can be in the form of gels, macroporous or sponge-like. Strongly acidic resins of the styrene-divinylbenzene type are sold, for example, under the following trade names: Duolite C20, Duolite C26, Amberlite 15, Amberlite IR-120, Amberlite 200, Dowex 50, K2611, K 2431.

The properties of these resins, in particular specific surface area, porosity, stability, swelling or shrinkage and ion-exchange capacity, can be varied by means of the production process.

The ion-exchange capacity is in the range from 1 to 2, in particular from 1.5 to 1.9, mol of $H^+$ per liter of moist resin (commercial).

In the process of the invention, preference is given to using macroporous resins, for example K 2431. The pore volume is from 30 to 60 ml/g, in particular from 40 to 50 ml/g (based on commercial resin moist with water).

The particle size of the resin is from 500 $\mu$m to 1 500 $\mu$m, in particular from 600 $\mu$m to 1 000 $\mu$m.

The particle size distribution can be relatively narrow or relatively broad. Thus, for example, ion-exchange resins having a very uniform particle size (monodisperse resins) can be used.

When using a plurality of reactors, these can be charged with resin of the same particle size or a different particle size (or particle size distribution).

In the case of reactors through which the reaction mixture flows at a high linear velocity, it may be advantageous to use a relatively large particle size to reduce the differential pressure, while in the case of reactors through which the reaction mixture flows at a low linear velocity, it may be advantageous to use a smaller particle size in order to achieve optimal conversion.

If desired, the ion-exchange resins can be used as shaped bodies, for example cylinders, rings or spheres.

There are a number of possible ways of preparing the catalysts having the desired activities. If the ion-exchange resin is in the H form, protons can be replaced by metal ions. If the resin is present as the metal salt, it can be treated with acids to replace metal ions by protons. In principle, this ion exchange can be carried out either in organic suspension or in aqueous suspension. Here, the ion-exchange resin is slurried with sufficient liquid for a readily stirrable suspension to be formed. A solution containing the desired ions is added thereto. After ion exchange is complete, the partly exchanged ion-exchange resin is washed and dried.

A preferred way of preparing the catalysts used in the process of the invention is replacement of protons by metal ions in an aqueous phase.

In the preparation of the catalyst, the ion-exchange resin is suspended in from one to ten times, in particular from one to three times, its volume of a solvent.

To prepare the solution of the desired ion to be added, it is advisable to choose a solvent which is miscible with the solvent in which the resin is suspended. Use of the same solvent is advantageous.

The ions with which the resin is to be loaded can be in the form of solutions of acids, hydroxides or salts of organic or inorganic acids. In the case of salts of polybasic acids, it is also possible to use acid salts. It is likewise possible to use compounds containing other organic groups, for example alkoxides or acetylacetonates.

Ion exchange is carried out while stirring in the temperature range from 10 to 100° C., in particular from 20 to 40° C.

The ion solution is added dropwise over a period of from 0.5 to 12 hours, in particular from 1 to 3 hours.

The exchange time (from the commencement of dropwise addition) is from 1 to 24 hours, in particular from 3 to 12 hours. After ion exchange, the catalyst is separated from the solution, e.g. by decantation or filtration, and is subsequently, if desired, washed with a solvent. It is advantageous to use the same solvent in which the catalyst was suspended.

The moist catalyst is dried, firstly to make it easier to handle (more free-flowing) and secondly to keep the contamination of the product with adhering solvent or its downstream products during the first days after starting-up the reactor low. Drying can be carried out under reduced pressure or in a stream of inert gas, for example in a stream of nitrogen. The drying temperatures are from 10 to 120° C., in particular from 40 to 80° C. The drying times are from 1 to 24 hours, depending on pressure and temperature.

Catalysts of differing activity can be prepared by the above-described procedure as a function of the degree of ion exchange, the ion type and the resin. A reactor can contain a mixture of resins of differing reactivity. It is likewise possible for catalysts of differing activity to be arranged in layers in a reactor. If use is made of more than one reactor, the individual reactors can be charged with catalysts having the same activity or different activities.

As starting material, it is possible to use pure isobutene or an isobutene-containing hydrocarbon mixture containing no further unsaturated compounds. When using pure isobutene, it is advisable to reduce the concentration by adding a solvent which is easy to separate off.

Industrial mixtures comprising isobutene include, for example, naphtha fractions from refineries, $C_4$ fractions from FCC plants or steamcrackers, mixtures from Fischer-Tropsch syntheses, mixtures from the dehydrogenation of butanes, mixtures from skeletal isomerization of linear butenes, mixtures formed by metathesis of olefins or other industrial processes.

Prior to use in the process of the invention, isobutene has to be separated from the other unsaturated compounds in these industrial mixtures. The isolation of isobutene from the $C_4$ fraction from a steamcracker is employed worldwide and will be described here by way of example. The isobutene is separated off in a process comprising essentially the following steps: the first step is removal of the major part of the butadiene. If butadiene can be readily marketed or is used in-house, it is separated off by extraction. Otherwise, it is selectively hydrogenated to linear butenes down to a residual concentration of about 2000 ppm, as described, for example, in EP 52 3482. Either method leaves a hydrocarbon mixture (raffinate I or hydrogenated crack C4) comprising the saturated hydrocarbons n-butane and isobutane together with the olefins isobutene, 1-butene and 2-butene. Isobutene can be separated from this mixture by reaction with methanol to form methyl tert-butyl ether (MTBE) or with water to form tert-butanol (TBA). Both MTBE and TBA can, in a reversal of their formation, be cleaved back into isobutene and methanol or water, as described, for example, in DE 100 20 943.

Optionally, raffinate I, hydrogenated crack $C_4$ or a hydrocarbon mixture of similar composition can be hydroisomerized in a reactive column. In this case, a mixture of isobutene and isobutane can be obtained as product from the top.

The process of the invention can be carried out in batch reactors or preferably continuously operating reactors as are customarily used for solid/liquid contact reactions. When using continuously operating flow reactors, it is usual but not absolutely necessary to employ a fixed bed. If a fixed-bed flow reactor is used, the liquid can flow upward or downward. Downflow of the liquid is usually preferred. Furthermore, the reactor can be operated with product recirculation or in a single pass.

When using tube reactors, the ratio of length to diameter of the catalyst bed can be varied, either by means of the geometric dimensions of the reactor or by means of its fill level. It is thus possible to achieve different empty tube velocities at a given quantity of catalyst and LHSV. Reactors in which part of the reaction mixture is recirculated, preferably after separating off the oligomers, can be operated at empty tube velocities of from 1 to 30 m/s, in particular from 2 to 20 m/s, very particularly preferably from 4 to 10 m/s. In reactors operated in a single pass, the empty tube velocities can be in the range from 0.1 to 20 m/s, in particular in the range from 0.8 to 8 m/s.

Owing to the reduced catalyst activity resulting from ion exchange, it is possible to employ lower velocities than in the case of an ion-exchange resin which has not been subjected to replacement of protons, since temperature peaks can be avoided more readily because of the lower activity.

In the case of reactors operating using product recirculation, preferably after the products have been separated off, the space velocity over the catalyst (LHSV) is from 0.5 to 15 $h^{-1}$, in particular from 1 to 10 $h^{-1}$, very particularly preferably from 2 to 5 $h^{-1}$. In the case of reactors operated in a single pass, the LHSVs are in the range from 1 to 50 $h^{-1}$, in particular from 5 to 30 $h^{-1}$.

The number of reactors connected in series in the process of the invention is in the range from 1 to 10, preferably from 1 to 4.

In a preferred process variant, the first reactor is operated with product recirculation and the subsequent reactors are operated in a single pass.

Each reactor can be operated adiabatically, polytropically or virtually isothermally. "Virtually isothermally" means that the temperature at any point in the reactor is not more than 10° C. higher than the temperature at the reactor inlet.

The temperatures at which the reactors are operated are in the range from 20 to 120° C., preferably from 40 to 100° C. The temperature is dependent on the activity of the catalyst (for example degree of ion exchange).

The reaction of the invention can be carried out at a pressure equal to or higher than the vapor pressure of the hydrocarbon feed mixture at the respective reaction temperature, preferably at a pressure below 40 bar. To avoid vaporization problems in the reactors, the pressure should be 2–4 bar higher than the vapor pressure of the reaction mixture.

The total conversion of isobutene depends on the type and amount of catalyst used, the prevailing reaction conditions and the number of reaction stages. For economic reasons, the isobutene conversion is kept in the range from 50 to 100%, preferably from 90 to 100%. In addition, it is advantageous to use hydrocarbons having an isobutene content of not less than 5%, preferably not less than 10%, in order to achieve a high space-time yield and a high $C_8$-olefin selectivity.

To achieve a very high selectivity of $C_8$-olefin formation, it is advisable to limit the concentration of oligomers, in particular $C_8$-olefins, in each reactor. Their concentration is in the range from 0 to 50%, in particular in the range from 0 to 30%. The concentration of oligomers can be limited by selection of operating parameters such as temperature or residence time. A further possibility is to keep the concentration of isobutene at the reactor inlet below 50%, in particular below 30%, by addition of a diluent. It is advantageous to use a diluent which is present in the starting material and can be recovered from the reaction mixture after partial or virtually complete reaction of the isobutene. A preferred embodiment of the process is therefore to separate the mixture leaving the reactor into a fraction comprising the oligomers and a second fraction comprising the diluent(s) and any unreacted isobutene. Part of the diluent together with the isobutene present therein is recirculated to the same reactor or a reactor upstream thereof and the other part is introduced into a downstream reactor or is worked up. In the case of a plurality of reactors connected in series, it is also possible for more than one oligomer separation step to be present. The oligomers which have been separated off (from one or more separation units) are separated into $C_8$-olefins, $C_{12}$-olefins and higher oligomers in a further distillation step.

If desired, the oligomerization can be carried out in a reactive distillation column containing the catalyst resin which has been subjected to ion exchange. Here, the above-mentioned temperature and pressure ranges apply. The oligomer mixture is obtained as bottom product. The top product comprises solvent and any unreacted isobutene. The work-up of these streams is carried out as described above.

It is also possible to carry out the process of the invention in a plant comprising one or more reactor(s) and a reactive distillation column.

The high-purity mixture of the two 2,4,4-trimethylpentene isomers prepared by the process of the invention can be hydroformylated to produce 3,5,5-trimethylhexanal. This aldehyde can be oxidized to the corresponding carboxylic acid or be hydrogenated to form the corresponding alcohol. 3,5,5-Trimethylhexanoic acid is used for the preparation of peroxides, lubricants and dryers. Furthermore, diisobutene is used for the alkylation of phenol or phenol derivatives. The alkylaromatics formed in this way are intermediates for the production of detergents. In addition, diisobutene is used for the alkylation of aromatic amines.

The process of the invention has the following advantages:

at virtually 100% conversion, the yield of 2,4,4-trimethylpentenes is from 80 to 85%. In addition, from 15 to 20% of higher oligomers, of which about 10% are $C_{12}$-olefins, are formed. The $C_8$ fraction has a 2,4,4-trimethylpentene content of over 99.7%, usually over 99.8%, and can, owing to its high purity, be used as starting material for chemical syntheses.

It is not necessary to add an auxiliary to control the product quality, which simplifies the process.

Since no auxiliaries are added, it is not necessary to separate them or their downstream products from the reaction mixture, in particular from the target products. This firstly saves costs for the auxiliaries and secondly simplifies separation. Since the product prepared according to the invention contains no traces of an extraneous substance (moderator), subsequent reactions are not adversely affected.

The following examples illustrate the invention but do not restrict its scope which is defined by the claims.

The preparation of the partially neutralized ion-exchange resins was carried out by reacting the acidic ion-exchange resin, suspended in water, with the calculated amount of an aqueous alkali metal hydroxide solution, as described by way of example in example 1.

EXAMPLE 1

Preparation of a Partially Neutralized Catalyst, Setting of the Acid Capacity

The ion exchanger used (Amberlyst 15 from Rohm & Haas) had an original acid capacity of 1.43 mol of $H^+$/l. To set the desired activity, 50% of the acid centers were neutralized.

For this purpose, 1000 ml of the ion-exchange resin were slurried in 1000 ml of deionized water and, while stirring vigorously, a solution of 28.6 g of sodium hydroxide (0.715 mol) in 500 ml of deionized water were added dropwise in the temperature range from 20 to 40° C. over the period of one hour. The mixture was stirred for another 5 minutes and the ion-exchange resin was then washed three times with 1000 ml each time of deionized water so that it was neutral. The subsequent capacity measurement on the partially neutralized ion exchanger gave a value of 0.715±0.03 mol of $H^+$/l. The catalyst was dried at 70° C. for 15 hours.

The oligomerization experiments (examples 2 to 5) were carried out in a jacketed laboratory tube reactor having a length of 2 m and an internal diameter of 2 cm. The temperature of the reactor could be regulated by means of a heat transfer fluid which was pumped through the reactor jacket. In all experiments, an isobutane/isobutene mixture was oligomerized at 23 bar.

EXAMPLE 2

Oligomerization Using a Catalyst Which has not Been Partially Neutralized (Comparative Example)

| Catalyst: | Amberlyst 15 |
|---|---|
| Jacket temp. (° C.): | 40 |
| Feed mixture | |
| isobutane (% by weight) | 83 |
| isobutene (% by weight) | 16 |
| n-butane (% by weight) | 1 |
| LHSV ($h^{-1}$) | 13 |
| Isobutene conversion (%) | 99.7 |
| Selectivities (%) | |
| diisobutene | 19 |
| triisobutene | 61 |
| higher oligomers | 19 |
| 2,4,4-Trimethylpentenes in the $C_8$ (% by weight) | 67 |

Owing to the high acid strength and capacity, the conversion is very high and the selectivity to dimers is very poor. Owing to transalkylation of the $C_8$-olefins during or after their formation, the desired trimethylpentenes make up only part of the $C_8$-olefins formed.

EXAMPLE 3

Oligomerization Using Partially Neutralized Catalyst (According to the Invention)

| Catalyst: | Amberlyst 15; 50% of $H^+$ replaced by $Na^+$ |
|---|---|
| Jacket temp. (° C.): | 40 |
| Feed mixture | |
| isobutane (% by weight) | 84 |
| isobutene (% by weight) | 15 |
| n-butane (% by weight) | 1 |
| LHSV ($h^{-1}$) | 13 |
| Isobutene conversion (%) | 78 |
| Selectivities (%) | |
| diisobutene | 63 |
| triisobutene | 33 |
| higher oligomers | 3 |
| 2,4,4-Trimethylpentenes in the $C_8$ (% by weight) | >99.9 |

Comparison with example 2 shows that although the partial neutralization reduces the conversion, it improves the selectivity to dimers under comparable reaction conditions.

The diisobutene is formed in high isomeric purity.

EXAMPLE 4

Oligomerization Using Partially Neutralized Catalyst (According to the Invention)

| Catalyst: | Amberlyst 15; 80% of $H^+$ replaced by $Na^+$ |
|---|---|
| Jacket temp. (° C.): | 110 |
| Feed mixture | |
| isobutane (% by weight) | 0 |
| isobutene (% by weight) | 100 |
| LHSV ($h^{-1}$) | 4 |
| Isobutene conversion (%) | 67 |
| Selectivities (%) | |
| diisobutene | 82 |
| triisobutene | 17 |
| higher oligomers | <1 |
| 2,4,4-Trimethylpentenes in the $C_8$ (% by weight) | >99.9 |

Replacement of 80% of the protons by sodium ions results in a significant reduction in the reaction rate, so that more severe conditions (higher temperature and/or higher isobutene concentration) are necessary for an industrially acceptable reaction rate. However, a selectivity to dimers better than that in example 3 is obtained despite the higher temperature.

EXAMPLE 5

According to the Invention

| Catalyst: | Amberlyst 15; 50% of $H^+$ replaced by $K^+$ |
|---|---|
| Jacket temp. (° C.): | 100 |
| Feed mixture | |
| isobutane (% by weight) | 45 |
| isobutene (% by weight) | 54 |
| n-butane (% by weight) | 1 |
| LHSV ($h^{-1}$) | 2 |
| Isobutene conversion (%) | 13 |
| Selectivities (%) | |
| diisobutene | 94 |
| triisobutene | 5 |
| higher oligomers (% by weight) | <1 |
| 2,4,4-Trimethylpentenes in the $C_8$ (% by weight) | >99.9 |

This example shows that more severe reaction conditions also make it possible to dimerize isobutene when $H^+$ is partly replaced by $K^+$.

Compared to the other examples, a very greatly improved selectivity to dimers is obtained.

The invention claimed is:

1. A process for preparing high-purity diisobutene comprising:
reacting isobutene or isobutene-containing hydrocarbon mixtures in the presence of a solid acidic ion-exchange resin containing sulfonic acid groups whose protons have been partly replaced by metal ions.

2. The process as claimed in claim 1, wherein from 30 to 90% of the protons have been replaced by metal ions.

3. The process as claimed in claim 1, wherein from 50 to 80% of the protons have been replaced by metal ions.

4. The process as claimed in claim 1, wherein the metal ions are alkali metal ions.

5. The process as claimed in claim 1, wherein the metal ions are sodium ions.

6. The process as claimed in claim 1, wherein the reaction is carried out at from 20 to 120° C.

7. The process as claimed in claim 6, wherein the reaction is carried out at from 40 to 100° C.

8. The process as claimed in claim 1, wherein the reaction is carried out in a liquid phase in a pressure range of from 5 to 40 bar.

9. A method of preparing 3,5,5-trimethyihexanoic acid comprising hydroformylation and subsequent oxidation of the diisobutene prepared according to the process of claim 1, wherein said diisobutene is part of a mixture comprising a $C_8$ fraction and higher oligomers, wherein the diisobutene content is over 99.7% of said $C_8$ fraction.

10. A method of preparing 3,5,5-trimethylhexanol comprising hydroformylation and subsequent hydrogenation of the diisobutene prepared according to the process of claim 1, wherein said diisobutene is part of a mixture comprising a $C_8$ fraction and higher oligomers, wherein the diisobutene content is over 99.7% of said $C_8$ fraction.

11. A method of alkylating phenols and/or aromatic amines comprising reacting the diisobutene prepared according to the process of claim 1 with phenols and/or aromatic amines, wherein said diisobutene is part of a mixture comprising a $C_8$ fraction and higher oligomers, wherein the diisobutene content is over 99.7% of said $C_8$ fraction.

12. A method of preparing 3,5,5-trimethylhexanoic acid comprising carrying out the process of claim 1, followed by hydroformylation and subsequent oxidation.

13. A method of preparing 3,5,5-trimethyihexanol comprising carrying out the process of claim 1, followed by hydroformylation and subsequent hydrogenation.

14. A method of alkylating phenols and/or aromatic amines comprising carrying out the process of claim 1, followed by reacting with phenols and/or aromatic amines.

* * * * *